United States Patent
Kirkpatrick

(10) Patent No.: US 9,797,877 B2
(45) Date of Patent: Oct. 24, 2017

(54) DIAGNOSTIC TOOL FOR COLORIMETRIC DETECTION OF ORGANIC RESIDUES

(71) Applicant: Robin Duncan Kirkpatrick, Johannesburg (ZA)

(72) Inventor: Robin Duncan Kirkpatrick, Johannesburg (ZA)

(*) Notice: Subject to any disclaimer, the term of this patent is extended or adjusted under 35 U.S.C. 154(b) by 37 days.

(21) Appl. No.: 15/022,018

(22) PCT Filed: Sep. 1, 2014

(86) PCT No.: PCT/IB2014/064173
§ 371 (c)(1),
(2) Date: Mar. 15, 2016

(87) PCT Pub. No.: WO2015/036893
PCT Pub. Date: Mar. 19, 2015

(65) Prior Publication Data
US 2016/0223502 A1    Aug. 4, 2016

(30) Foreign Application Priority Data

Sep. 16, 2013 (ZA) .................... 2013/06966
Apr. 4, 2014 (ZA) .................... 2014/02575

(51) Int. Cl.
*G01N 33/18* (2006.01)
*G01N 21/75* (2006.01)
(Continued)

(52) U.S. Cl.
CPC ......... *G01N 33/1826* (2013.01); *G01N 21/75* (2013.01); *G01N 33/52* (2013.01);
(Continued)

(58) Field of Classification Search
CPC .. G01N 21/78; G01N 33/1826; G01N 21/251; G01N 21/75; G01N 21/77; G01N 33/52; Y02W 10/37
See application file for complete search history.

(56) References Cited

U.S. PATENT DOCUMENTS

| | | | |
|---|---|---|---|
| 2,608,533 A | 8/1952 | Carson et al. | |
| 5,238,846 A * | 8/1993 | Aucutt | G01N 31/22 436/164 |
| 2010/0112680 A1* | 5/2010 | Brockwell | A61B 5/07 435/287.9 |

FOREIGN PATENT DOCUMENTS

| | | |
|---|---|---|
| JP | 55-15922 | 2/1980 |
| WO | WO 2008/088872 | 7/2008 |

OTHER PUBLICATIONS

Sinha VR, Kumar RV, Utility of an oxidation reaction for the spectrophotometric determination of acarbose in controlled release tablets at various simulated gastrointestinal media. Acta Pol Pharm. Jan.-Feb. 2012; 69(1):23-32. Section 'Experimental'.

(Continued)

*Primary Examiner* — Jennifer Wecker
(74) *Attorney, Agent, or Firm* — Nixon & Vanderhye P.C.

(57) ABSTRACT

This invention relates to a semi-quantitative diagnostic tool and a method for using the same to verify the efficacy of cleaning-in-place procedures in eliminating carbohydrate-based, organic residues from product contact surfaces in food, beverage and pharmaceutical manufacturing, processing and packaging facilities. The diagnostic tool comprises a permanganate-based colorimetric indicator formulation and a translucent assay container for containing the permanganate-based colorimetric indicator formulation. The diagnostic tool is characterized therein that the permanganate-based colorimetric indicator formulation is admixed with a product sample to be tested so that the admixed permanganate-based colorimetric indicator formulation undergoes a colorimetric reaction in the presence of organic residues in (Continued)

the product sample, the arrangement being such intensity of the colorimetric reaction displayed provides a semi-quantitative determination of a concentration of organic residue dissolved or suspended in the product sample.

34 Claims, 3 Drawing Sheets

(51) Int. Cl.
    *G01N 21/78*     (2006.01)
    *G01N 33/52*     (2006.01)
    *G01N 31/22*     (2006.01)
    *G01N 21/77*     (2006.01)
    *G01N 21/25*     (2006.01)

(52) U.S. Cl.
    CPC ........... *G01N 21/251* (2013.01); *G01N 21/77* (2013.01); *G01N 21/78* (2013.01); *Y02W 10/37* (2015.05)

(56) References Cited

OTHER PUBLICATIONS

Crimi M., Ko S. Control of manganese dioxide particles resulting from in situ chemical oxidation using permanganate. Chemosphere, Feb. 2009; 74(6): 847-53. doi:10.1016/j.chemosphere.2008.09.074. Epub Nov. 25, 2008, Fig 2.

International Search Report for PCT/IB2014/064173 mailed Nov. 24, 2014.

\* cited by examiner

DIAGNOSTIC TOOL FOR COLORIMETRIC DETECTION OF ORGANIC RESIDUES

This application is the U.S. national phase of International Application No. PCT/IB2014/064173 filed Sep. 1, 2014 which designated the U.S. and claims priority to South African Application No. ZA2013/06966 filed Sep. 16, 2013 and to South African Application No. ZA2014/02575 filed Apr. 4, 2014, the entire contents of each of which are hereby incorporated by reference.

FIELD OF THE INVENTION

This invention relates to a semi-quantitative diagnostic tool and a method for using the same to verify the efficacy of cleaning-in-place procedures in eliminating organic residues from product contact surfaces in food, beverage and pharmaceutical manufacturing, processing and packaging facilities. The invention extends to use of the diagnostic tool for diagnosing organic compounds that are associated with microbial biofilms in treated process water in food, beverage and pharmaceutical industries, as well as potable water destined for human consumption.

BACKGROUND TO THE INVENTION

CIP and SIP Procedures Applied in Food, Beverage and/or Pharmaceutical Manufacturing, Processing and/or Packaging Facilities The term Cleaning-in-Place ("CIP") has been adopted as the determinant descriptive that refers to a process when an item of immovable food, beverage or pharmaceutical manufacturing, processing and/or packaging equipment may be deemed to be both clean and sanitary. The reference to "food, beverage and/or pharmaceutical manufacturing, processing and/or packaging system and/or equipment" in this specification refers to any given product type and includes all raw, intermediate and final product contact surfaces where the potential for accumulation of product residue is possible, including, but not limited to, fixed and removable components of the ingredient and/or product storage, manufacturing, processing and/or packaging system or subsystems thereof, including related equipment.

The measures to verify the efficacy of a CIP process have predominantly been aligned to the assessment of the sanitary or microbial contamination status of the equipment after a CIP procedure, and these measures have become the indirect yardstick for determining whether the cleaning component of the CIP procedure has been effective in terms of removal of residual product soils. However, because industrial food, beverage and pharmaceutical processors have adopted the verification of the cleaning and sanitizing processes to the tools and measures directly associated with determining the presence of microbial contaminants, this approach potentially permits tenacious soils (organic and inorganic residues), such as flavourants, colourants and complex biological materials, to persist in the manufacturing, processing and/or packaging infrastructure, albeit in a sanitized or sterile state.

Notwithstanding the capacity of these organic and inorganic residues to vest and consolidate in difficult-to-clean places, they also serve as the foundation for a biofilm matrix to form, wherein a microbial consortium will readily proliferate. In addition, the persistence of tenacious soils, such as carbohydrate or oil-based flavourants and colourants, will compromise further batch-packaging and overall product integrity. The persistence of organic soils provides a nutritional platform for microbes to flourish and incomplete cleaning will inevitably result in widespread microbial contamination, concomitant product spoilage and premature deterioration. Furthermore, this largely undetected microbial contamination of consumer products may also increase the potential for contamination of such consumer products with microbes which are human pathogens and which would have heightened adverse public health implications.

By actively realigning the cleaning and sanitization process of a given industrial food, beverage and/or pharmaceutical processor to the recognition of the likely profile of residual soils that would be encountered in all equipment, and then tailoring the choice of cleaning and sanitizing remedies best suited to optimizing the CIP and Sanitizing-in-Place ("SIP") procedures, one has a substantially greater likelihood of delivering consistently reliable CIP and SIP procedural outcomes.

It is known in the industry that, to use dedicated colorimetric indicators to evaluate the presence or absence of organic soils in various intermediate rinse solutions, is a critical step in verifying whether a detergent agent used has effectively removed residual soils, prior to embarking upon a subsequent sanitizing intervention. Such colorimetric indicators also serve to guide the choice of detergent agent relative to a product soil profile and equipment design, the application protocol and most importantly, the profile of organic and inorganic soils likely to persist after production and packaging.

Current colorimetric indicator assays for organic compounds rely primarily on formulations using permanganate chemistry and its well established reactivity when mixed with organic soils in an alkaline environment. However, the problems associated with permanganate stability are also well established. As a potent oxidizing agent, permanganate's stability, once exposed to environmental conditions (primarily oxygen), results in a rapid breakdown of the permanganate molecule with rapid loss of reliable colour-based reactivity when mixed with organic compounds. It is for this reason that all current permanganate colorimetric indicators are available as solid or powder formulations only, packaged in and under corrosion, light, atmosphere and moisture sensitive materials and conditions. All formulations are applied on-site to process water used for cleaning of food, beverage and pharmaceutical equipment and do not display any extended stability once re-constituted with water.

Previous patents using permanganate-based chemistry, such as Thonhauser et. al. (U.S. Pat. No. 8,083,966) and Fischer (U.S. Pat. No. 7,867,339), have described products and procedures where the permanganate molecule forms a component of a cocktail of cleaning and disinfecting compounds. The reconstituted formulation is applied into the internal reticulation of a beverage processing and packaging system and the colour changes in the cleaning and disinfecting solution are a reflection of the efficacy of the latter compounds in effecting the required cleaning and sanitation of the equipment.

This invention serves to make available a reliable colorimetric indicator diagnostic tool, which has an extended shelf life when stored under optimal storage conditions. Moreover, the invention seeks to provide a diagnostic tool and a method of using the same that will re-educate plant operators of the need to separate CIP processes from SIP processes, and which will readily assist in evaluating and improving current CIP practices, as well as trouble-shooting instances where inconsistent packaged product quality may result in compromised brand integrity and equity.

Historical reliance on diagnostic tests (e.g. Clinistix) and ATP systems have been shown not to be repeatable in guaranteeing optimal removal of organic residues from food, beverage or pharmaceutical manufacturing, processing and/or packaging equipment. To date there is no dedicated and reliable measure to quantify whether a CIP process has been effective in removing such organic residues.

Microbial Biofilms

The term "microbial biofilm" describes the presence of a variety of microbial cells which are adherent to a contact surface and enclosed in a matrix of Extracellular Polymeric Substances ("EPS") in an aqueous environment. Biofilm has been reported to comprise of consortia of micro-colonies of different species of microbial cells (≤15% by volume) and a non-cellular matrix of various predominantly organic components (≤85% by volume) which confers structural stability. The structure of a matrix of EPS has been shown to comprise primarily of polysaccharides and, to a lesser extent, proteins, nucleic acids, peptidoglycan and lipids. The polysaccharides have been shown to consist of homo-polymers, such as cellulose, as well as a wide variety of monosaccharide carbohydrate compounds, including glucose, fructose, galactose and mannose, amongst others. Teichoid acids, comprising glycerol and glucose, are also encountered.

The significance of a confirmed biofilm presence in any aqueous environment is that microbial cells, or microbes, present in the EPS matrix serve as a source of continuous microbial contamination for the aqueous system. In addition, impermeability of the EPS matrix confers a significant degree of protection for the varied microbial populations against biocidal agents that may be used to control microbes in the same environment. Finally, the EPS matrix provides a nutritional platform to support and promote the growth of various microbes.

The biofilm structure and appearance is dictated by many factors, including the nutritional profile of the aqueous environment, oxygen tension, as well as the flow rate of the liquid across the surface of the biofilm. As biofilms grow and mature, portions will break free from a parent biofilm, thus spreading both microbes and aspects of the EPS matrix to other aspects of the aqueous liquid system.

Water used in the preparation of CIP procedures, SIP procedures and final rinse solutions in food, beverage and pharmaceutical industries, may be sourced from municipal supplies or alternatively prepared on-site in water treatment plants, specifically geared to preparing water solutions of known quality and sanitary status. In these water treatment facilities, the presence of biofilm serves to reduce the efficiency and yield of process equipment such as sand filters, ultra- and nano-filtration and reverse osmosis membrane systems. In addition, the continuous presence of microbial biofilms would serve to contaminate the treated water with microbes.

Where the aqueous solutions containing dislodged and free-floating microbes and aspects of the EPS matrix are used in cleaning and sanitation procedures in food, beverage or pharmaceutical manufacturing, processing and/or packaging equipment and facilities, there is a significantly heightened risk of both further downstream contamination of the manufacturing, processing and/or packaging equipment with organic soils and microbes, as well as microbial spoilage of food, beverage and pharmaceutical products produced and packaged with the equipment.

Moreover, as part of a filtration process to treat raw water from open water bodies (such as seawater, dams, lakes, and the like) for the production of potable water for human consumption, the specific requirement to control dissolved organic compounds is an inevitable consequence of the overall process. These complex organic compounds comprise primarily of humic and fulvic acids and differ substantially in size and molecular mass from 300 000 to 2000d respectively.

Membrane filtration systems used in potable water treatment plants are designed to exclude these organic compounds from the final water product and selectively to remove high molecular mass compounds first through ultra-filtration systems ("UF"), which allows smaller molecular mass organic compounds to pass through the membranes for further processing in subsequent filtration stages. However, the presence of progressively increasing concentrations of low molecular mass organic compounds in intermediate processed water streams provide the fundamental nutritional building blocks necessary to support and sustain microbial growth in the system. This results in incremental bio-fouling of the membrane filtration systems and all supporting infrastructure.

The invention seeks to provide a diagnostic tool and a method of using the same as a pre-screening aid to verify the absence of organic contaminants normally associated with biofilm from prepared rinse water prior to its use as a final rinse solution after both CIP and SIP procedures. The invention further seeks to provide a diagnostic tool and an associated method for use thereof to identify the molecular mass of organic contaminants in a water sample.

SUMMARY OF THE INVENTION

According to the invention, there is provided a semi-quantitative diagnostic tool adapted to indicate the presence of organic residues in a product sample wherein the diagnostic tool includes a colorimetric indicator which is adapted to undergo a colour change when brought into contact with organic residues, the diagnostic tool comprising — a permanganate-based colorimetric indicator formulation comprising a dry permanganate compound, wherein the dry permanganate compound is stabilized with a chemically inert anhydrous polyphosphate and/or orthophosphate stabilizer compound and a hydroxide-based buffer compound, and wherein the quantity of dry permanganate compound in the permanganate-based formulation is predetermined such that a particular colour reaction is standardized according to a concentration of organic residues in the product sample; and a translucent assay container for containing the permanganate-based colorimetric indicator formulation;

the diagnostic tool being characterized therein that the permanganate-based colorimetric indicator formulation is admixed with a fixed sample volume of the product sample in the assay container so that the admixed permanganate-based colorimetric indicator formulation undergoes a colorimetric reaction in the presence of organic residues in the product sample; and the diagnostic tool further being characterized therein that intensity of the colorimetric reaction displayed when an organically soiled product sample is admixed with the permanganate-based colorimetric indicator formulation provides a semi-quantitative determination of a concentration of organic residue dissolved or suspended in the product sample.

In one embodiment of the invention, the diagnostic tool may be used to indicate the presence of organic residues in food, beverage and pharmaceutical manufacturing, processing and packaging equipment.

In an alternative embodiment of the invention, the diagnostic tool may be used to indicate the presence of organic residues in water contaminated with biofilm. In particular, the diagnostic tool may be used to indicate the presence of organic residues from biofilm in prepared rinse water, particularly prior to its use as a final rinse solution after both CIP and SIP procedures. More particularly, the diagnostic tool may be used to indicate the presence of EPS found in biofilms, as well as further components associated with an EPS matrix, such as polysaccharides, cellulose, glycerol, glycerine and proteins. In this application the diagnostic tool may be used to verify efficacy of both CIP and SIP procedures to remove residual organic soils specifically associated with food, beverage and pharmaceutical equipment. The proposed procedure of sampling rinse water both before and after CIP and SIP procedures will also assist to exclude "false-positive" results that may arise as a result of secondary soiling of the manufacturing, processing and packaging equipment with biofilm contaminated rinse water.

The diagnostic tool further may include a cationic sequestering agent for further stabilizing the permanganate-based colorimetric indicator formulation against oxidative degradation. The cationic sequestering agent may be calcium. The permanganate-based colorimetric indicator formulation may include equal concentrations of cationic sequestering agent and dry permanganate compound. It will be appreciated that permanganate is reduced to manganate in the presence of hydroxyl, which is essential to the overall colorimetric reaction. Addition of divalent cations ($Ca^{++}$) precipitates/sequesters degraded indicator manganate molecules, thus preventing further autocatalysis of the permanganate molecules.

The dry permanganate compound may be formulated with one, or a combination of, potassium permanganate ($KMnO_4$), ammonium permanganate ($NH_4MnO_4$), calcium permanganate ($Ca(MnO_4)_2$), sodium permanganate ($NaMnO_4$), and/or silver permanganate ($AgMnO_4$). Preferably, the permanganate compound may be formulated with potassium permanganate ($KMnO_4$).

The permanganate-based colorimetric indicator formulation may be prepared under alkaline conditions.

The permanganate-based colorimetric indicator formulation may be compressed into a pellet or tablet form before it is introduced into the assay container. Alternatively, the permanganate-based colorimetric indicator formulation may be packaged in suitable packaging.

The chemically inert anhydrous polyphosphate and/or orthophosphate stabilizer compound used for pre-stabilizing the dry permanganate compound may be one, or a combination of, potassium dihydrogen orthophosphate and/or disodium hydrogen orthophosphate.

The hydroxide-based buffer compound with which the dry permanganate compound is buffered may be one, or a combination of, sodium hydroxide, magnesium hydroxide and/or potassium hydroxide.

The assay container may have a fixed sampling volume of typically 100 ml.

The diagnostic tool may be characterized therein that the permanganate-based colorimetric indicator formulation is introduced into the assay container under conditions that are devoid of oxygen and moisture. For this reason, the assay container is purged with one, or a combination of, argon, helium, or nitrogen. The assay container is preferably purged with nitrogen to prevent oxidation and/or hydrolysis of the permanganate-based colorimetric indicator formulation before the permanganate-based colorimetric indicator formulation is exposed to a product sample.

The assay container may be sealed after receipt of the permanganate-based formulation. In particular, the assay container may include a tamper seal to indicate when sealing of the assay container has been compromised.

The quantity of dry permanganate compound in the permanganate-based colorimetric indicator formulation is predetermined so as to yield particular and repeatable colour reactions when exposed to fixed concentrations of organic residues in a product sample. The colour reaction of the permanganate-based colorimetric indicator formulation is reliably predictable and repeatable in view of the fact that the volume of product sample is prescribed by the fixed volume of the assay container and a proportionately measured dose of permanganate-based colorimetric indicator formulation is added to each assay container.

The permanganate-based colorimetric indicator formulation may be stored under conditions of reduced temperature and a dark environment to exclude oxidative effects of direct sunlight or alternative sources of oxidative UV radiation. The colour indicator functionality of the admixed permanganate-based colorimetric indicator formulation is the result of an oxidative and endothermic hydrolytic reaction of the permanganate-based colorimetric indicator formulation. For this reason, the permanganate-based colorimetric indicator formulation is stored under temperature conditions of less than 10° C., and preferably at 4° C.

The permanganate-based colorimetric indicator formulation may further be characterized therein that it excludes all organic compounds, thus excluding the possibility of an inherent "false positive" reaction in use.

The diagnostic tool further may include a standard colour chart illustrating a series of colour reactions wherein each colour reaction corresponds to a specific concentration of organic residue in a product sample. Once a product sample is brought into contact with the permanganate-based colorimetric indicator formulation, the intensity of the resultant colour reaction is directly contrasted against the colour chart to diagnose a semi-quantitative concentration of organic residue present in the product sample.

The diagnostic tool may include a set of standard colour charts with each colour chart illustrating a series of colour reactions and wherein different colour charts correspond to different types of product samples encountered in different applications in the food, beverage and pharmaceutical industry. In particular, the arrangement may be such that for each type of product sample, the intensity of a colour reaction when that product sample is brought into contact with the permanganate-based colorimetric indicator formulation is directly contrasted against the colour chart for that particular type of product sample to diagnose a semi-quantitative concentration of organic residue present.

The diagnostic tool also may include an untreated control comprising an assay container that is purged with an inert or noble gas, and including the permanganate-based colorimetric indicator formulation, wherein the permanganate-based colorimetric indicator formulation is admixed with a volume of demineralized water of known purity to undergo a colorimetric reaction, the arrangement being such that the colorimetric reaction displayed when a product sample is admixed with the permanganate-based formulation of a test assay is contrasted against the colorimetric reaction of the untreated control to determine the presence or not of organic residues in the product sample.

The diagnostic tool may be adapted to diagnose a concentration of organic residues in a product sample of as low as ≤1 ppm.

It will be appreciated that both severity of a colorimetric reaction and time duration required for a complete colorimetric reaction to occur after an organically soiled product sample is admixed with the permanganate-based colorimetric indicator formulation is dependent on the concentration of organic residues present in the product sample. The diagnostic tool is adapted such that after 5 minutes from the time when an organically soiled product sample is admixed with the permanganate-based colorimetric indicator formulation, a resultant colorimetric reaction will reliably diagnose a concentration of organic residues in a product sample of as low as ≤1 ppm.

According to a second aspect of the invention there is provided a permanganate-based colorimetric indicator formulation which is adapted to undergo a colour change when brought into contact with organic residues in a product sample, the permanganate-based colorimetric indicator formulation comprising a dry permanganate compound, wherein the dry permanganate compound is stabilized with a chemically inert anhydrous polyphosphate and/or orthophosphate stabilizer compound and a hydroxide-based buffer compound, and wherein the quantity of dry permanganate compound in the permanganate-based formulation is predetermined such that a particular colour reaction is standardized according to a concentration of organic residues in the product sample.

According to a third aspect of the invention there is provided a method of obtaining a semi-quantitative indication of the presence or absence of organic residues in a product sample, the method comprising the steps of —
  providing a diagnostic tool comprising —
    a permanganate-based colorimetric indicator formulation comprising a dry permanganate compound, wherein the dry permanganate compound is stabilized with a chemically inert anhydrous polyphosphate and/or orthophosphate stabilizer compound and a hydroxide-based buffer compound, and wherein the quantity of dry permanganate compound in the permanganate-based colorimetric indicator formulation is predetermined such that a colour reaction is standardized according to a concentration of organic residues in a product sample; and
    a translucent test assay container for containing the permanganate-based colorimetric indicator formulation,
  providing either one or both of a standard colour chart on which a series of colour reactions each correspond to a concentration of organic residue, and/or an untreated control;
  collecting a fixed sample volume of product sample and admixing it with the permanganate-based colorimetric indicator formulation in the test assay container such that the permanganate-based colorimetric indicator formulation undergoes a colorimetric reaction in the presence of organic residues in the product sample; and
  contrasting presence and/or intensity of the colorimetric reaction against either one or both of the colour chart or untreated control to diagnose a semi-quantitative concentration of organic residue present in the product sample.

The method may include the step of collecting product sample from a food, beverage and/or pharmaceutical manufacturing, processing and packaging equipment after a CIP process or cycle and before the step of introducing a SIP process or cycle so as to verify the efficacy of the CIP process or cycle as mandated by a specific food and/or beverage producer.

Additionally, or alternatively, the method may include the step of collecting product sample from prepared rinse water, particularly prior to its use as a final rinse solution after both CIP and SIP procedures, so as to indicate the presence or absence of EPS found in biofilms, as well as further components associated with an EPS matrix, such as polysaccharides, cellulose, glycerol, glycerine and proteins.

The invention extends to the use of a diagnostic tool as hereinbefore described for detecting and semi-quantifying organic residues in rinse effluent in food, beverage and pharmaceutical manufacturing, processing and packaging applications, systems and equipment. In particular, the invention extends to the use of a diagnostic tool as hereinbefore described for detecting and semi-quantifying carbohydrate-based organic residues in rinse effluent in systems and equipment for processing brewed beverages, fermented beverages, fruit and vegetable beverages, tea and coffee beverages, flavoured water products, carbonated soft drinks, sport drinks, combinations thereof, or pharmaceuticals.

The invention extends to the use of a diagnostic tool as hereinbefore described for detecting a presence of potent oxidising chemical residues in rinse effluent in food, beverage and pharmaceutical manufacturing, processing and packaging applications, systems and equipment.

The invention extends to the use of a diagnostic tool as hereinbefore described for verifying cleaning procedures of "point-of-use" beverage dispensers installed in, but not limited to, retail outlets and equivalent hospitality venues.

The invention extends to the use of a diagnostic tool as hereinbefore described for identifying and isolating a source of organic contamination in specific areas of food, beverage and pharmaceutical manufacturing, processing and packaging systems and equipment, to remedy the organic contamination at that point and thereby to optimize production efficacy through enhanced processing and packaging asset utilization.

The invention extends to the use of a diagnostic tool as hereinbefore described for indicating the presence or absence of organic residues from biofilm in prepared rinse water, particularly prior to its use as a final rinse solution after both CIP and SIP procedures. More particularly, the diagnostic tool may be used to indicate the presence or absence of EPS found in biofilms, as well as further components associated with an EPS matrix, such as polysaccharides, cellulose, glycerol, glycerine and proteins. In this application the diagnostic tool may be used to verify efficacy of both CIP and SIP procedures to remove residual organic soils specifically associated with food, beverage and pharmaceutical products. The invention extends to the use of the diagnostic tool according to the invention for sampling rinse water both before and after CIP and SIP procedures in order to exclude "false-positive" results that may arise as a result of secondary soiling of the manufacturing, processing and packaging equipment with biofilm contaminated rinse water.

The invention extends to the use of a diagnostic tool as hereinbefore described for precipitating organic contaminants from a water sample such that the extent of organic precipitate is an indication of the molecular mass of organic contaminants present in the water sample.

BRIEF DESCRIPTION OF THE DRAWINGS

The invention will now further be described by way of examples only and with reference to the following figures in which—

SPECIFIC EMBODIMENTS OF THE INVENTION

The invention will now further be described by way of examples only and with reference to the foregoing figures.

Figure 2:
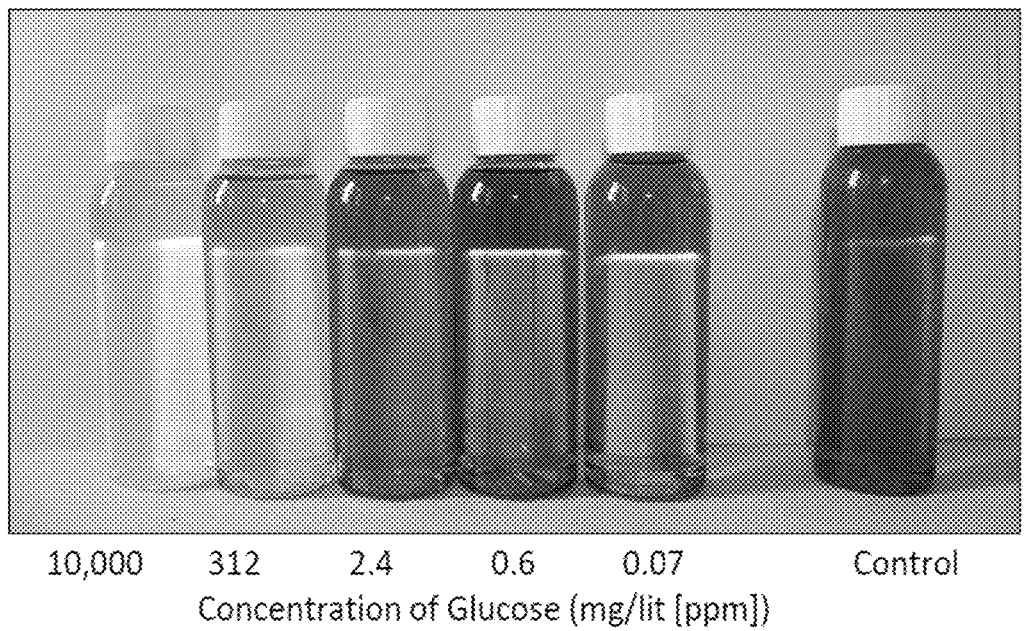
FIG. 2 is a detailed image of the extent of colour changes that the diagnostic tool undergoes, together with a correlation to the concentration of a carbohydrate-based compound (i.e. glucose monohydrate). Equivalent sensitivities to other carbohydrate-based compounds (i.e. sucrose and maltose) were also verified.
Figure 3:
FIG. 3 details a range of colour changes resulting from a progressive dilution of a carbohydrate-based compound (i.e. glucose monohydrate). The dilution series ranged from 10,000 ppm through to 0.07 ppm of the glucose solution and was reliably sensitive to less than 1 ppm.

FIGS. 2 and 3 each disclose a series of translucent assay containers that are used in the diagnostic tool according to the invention. Each assay container is purged with an inert or noble gas, receives a tablet or pellet of the permanganate-based colorimetric indicator formulation according to the invention, is closed and sealed with a tamper seal.

At a point of use and after a CIP process is completed, the tamper seal of the assay container is broken and a fixed sample volume of a product sample, such as rinse effluent, from the food, beverage and pharmaceutical manufacturing, processing and packaging equipment is admixed with the permanganate-based colorimetric indicator formulation in the assay container. The permanganate-based colorimetric indicator formulation undergoes a colorimetric reaction in the presence of organic residues in the product sample, such that degree of the colorimetric reaction and time duration required for a complete colorimetric reaction to occur after an organically soiled product sample is admixed with the permanganate-based colorimetric indicator formulation is dependent on the concentration of organic residues present in the product sample.

Figure 1:
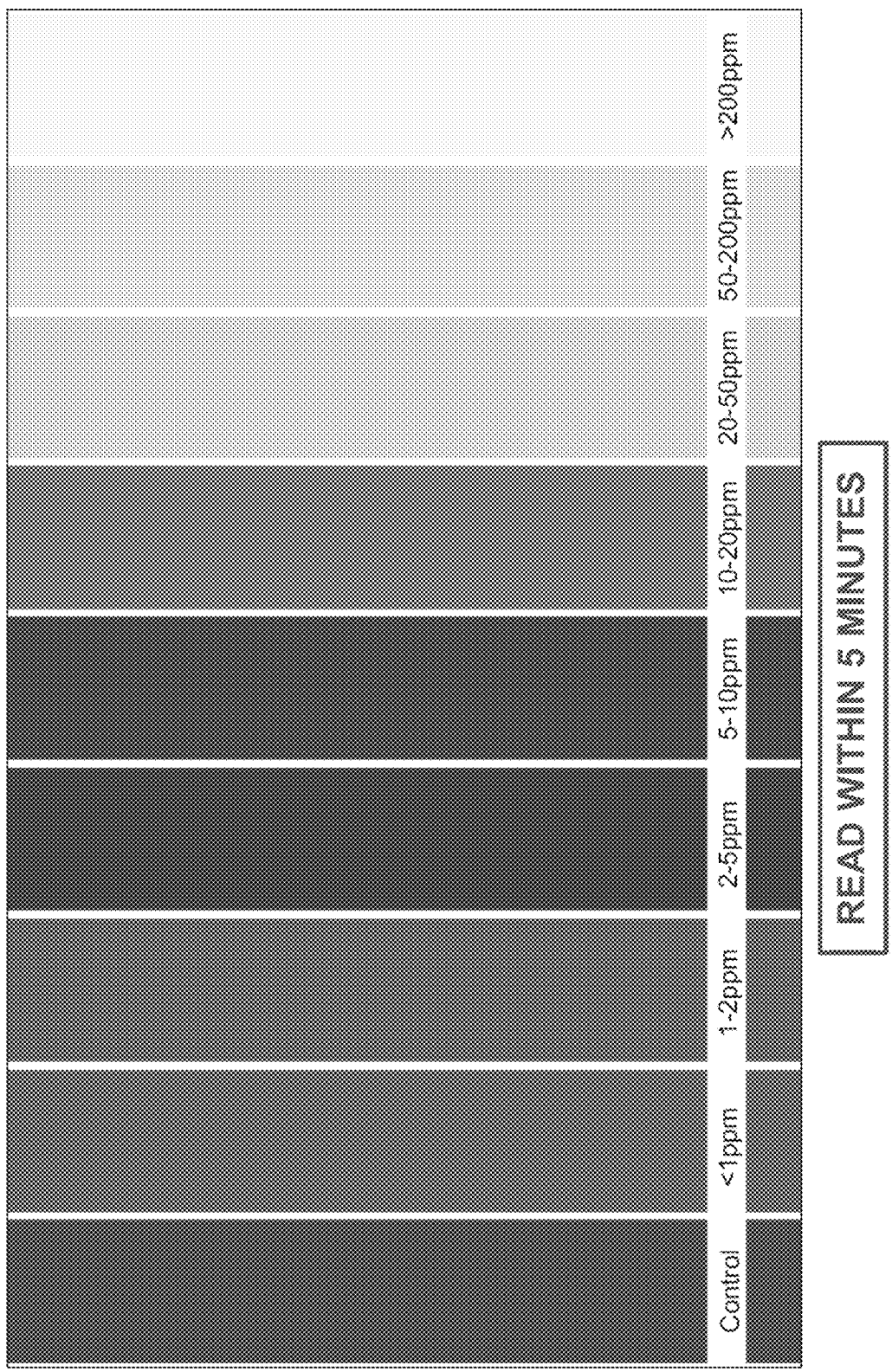
FIG. 1 is one example of a standard colour chart used in the diagnostic tool according to the invention.

After 5 minutes, the colorimetric reaction in the assay container is contrasted against the untreated control to diagnose the presence or not of organic residues in the product sample. Alternatively or additionally, the colorimetric reaction in the assay container is contrasted against the standard colour chart of FIG. 1 to semi-quantify the concentration of organic residues in the product sample.

EXAMPLE 1

In one embodiment of the invention, the permanganate-based colorimetric indicator formulation may comprise of the following:

| | % (m/m) | Range-% (m/m) |
|---|---|---|
| Potassium hydroxide | 0.614 | 0.606-0.628 |
| Sodium hydroxide | 0.123 | 0.120-0.125 |
| Anhydrous orthophosphate buffers | 0.230 | 0.226-0.235 |
| Divalent cationic sequestrant | 0.020 | 0.019-0.021 |
| Potassium permanganate | 0.021 | 0.020-0.021 |
| Silica binding agent | 0.001 | 0.0005-0.0015 |
| Total | 1 | |

Nitrogen gas - technical grade 100 ml of 98% purity grade by volume

EXAMPLE 2

A comparative test was conducted to evaluate the capacity of the permanganate-based colorimetric indicator formulation to detect the presence of organic soils in an effluent stream of a final rinse solution of a beverage filler system after both cleaning (CIP) and sanitization (SIP) processes. As a baseline standard, the permanganate-based colorimetric indicator formulation was admixed in a prescribed proportion with a treated water sample of known purity. The intensity of this specific colour reaction was contrasted against the colour reaction that developed after the effluent final rinse solutions were admixed with the permanganate-based colorimetric indicator formulation in directly equivalent proportions. The substantive dose and time-based colour differences that were associated with the presence of organic residues in the final rinse solutions confirmed that the diagnostic tool and method provided a reliable and repeatable measure to detect failures in the CIP procedure.

EXAMPLE 3

A laboratory based trial evaluating the variations of colour intensity displayed after exposure of sample volumes of different concentrations of two carbohydrate (maltose and glucose) solutions and a fixed measure of the permanganate-based colorimetric indicator formulation was conducted with assessments of colour changes at fixed time periods after admixture. There was a distinctive and reliably repeatable colour change associated with the different concentrations of the two carbohydrate solutions, and the intensity of the colour change relative to the untreated control could be directly correlated to the specific concentration of carbohydrate in the test solution.

EXAMPLE 4

During on-going trials at a brewery to validate the capacity of the diagnostic tool according to the invention to detect organic residues in the final rinse solutions from process equipment after a cleaning and sanitising procedure, it has been established that the diagnostic tool was also significantly effective in detecting the presence of potent oxidising chemical residues in the final rinse solutions and hence the process equipment.

Positive reactions associated with the residual oxidising sanitiser—in this case hydrogen peroxide—yielded a "false positive" result and would ordinarily diminish the reliability of the diagnostic tool to solely detect residual organics in the rinse water.

The means to circumvent the potential "false positive" result due to the presence of the peroxide residues, is to evaluate the pH of the final rinse solution to exclude the presence of these residual chemical oxidant residues. This simple measure of pH determination can be conducted with pH indicator tape, Universal Indicator solution, or laboratory based pH measurement probes.

While the presence of potent oxidising (peroxide based) chemical compounds (even in the presence of organic residues) will exclude any definitive determination of organic contaminants, it does provide an extremely valuable tool for the detection of residual CIP chemicals that may not have been adequately rinsed from the process equipment. The significance of these oxidant residues on the product contact surfaces of the process equipment has significant product quality implications. Where sensitive beverages (or other equivalently sensitive product types, such as in food or pharmaceuticals applications) are exposed to acidic oxidant compounds, the stability of these products would be substantially compromised with potential risk to the optimal product profile (flavour, odour and foaming quality, etc.), as well as the prescribed minimum shelf life stability.

What has evolved from on-going evaluations of the diagnostic tool performance sensitivity, is that aside from validating the efficacy of the diagnostic tool for detection of residual organics, it is now relevant that the technology is also a reliable indicator for the detection of potent oxidising residues in final rinse water, and by implication the adverse presence of the same on the process equipment.

Figure 4:
FIG. 4 displays the colour differences in the diagnostic tool of the invention when a contaminated water sample with high molecular mass organic compounds (e.g. humic acids) is admixed with the colorimetric indicator formulation (i.e. sample on the left); versus the situation when a contaminated water sample with low molecular mass organic compounds (e.g. fulvic acids) is admixed with the colorimetric indicator formulation (i.e. sample on the right).

With reference to FIG. 4, the diagnostic tool according to the invention has been shown to be sensitive to the presence of organic compounds in both raw and processed water samples. In particular, the magnitude of the colour reaction displays a clear correlation relative to the molecular mass of the organic compound present in the water samples.

The diagnostic tool does not display any significant colour reactions in the presence of high molecular mass compounds (i.e. humic acids), but as the concentration of low molecular mass organic compounds (i.e. fulvic acids) increases through a filtration process, the diagnostic tool displays progressively more positive colour changes corresponding to the increasing concentration of readily available nutrients which will support microbial growth and concomitant biofouling. Depending on the concentration of the low molecular mass organic compounds in the water solution, the colour changes displayed after exposure to the diagnostic tool display a correlation in terms of the colour change over time.

In addition, the formulation of the diagnostic tool comprises a potent oxidant compound which has the capacity to precipitate complex organic compounds, resulting in separation of such compounds from the water fraction of a sample. The quantity of the organic compounds can also be qualified according to the amount of precipitate that forms over time and a correlation can be drawn between the degree of the colour change and the type and extent of precipitate that forms after exposure to the diagnostic tool.

The pink colour of the water sample with humic acids (sample on the left in FIG. 4) confirms that there is a high concentration of predominantly high molecular mass organic compounds and the extensive precipitate corresponds with this result. Conversely, when the high molecular mass organic compounds are filtered out and the residual organic compounds comprise predominantly of low molecular mass compounds (i.e. fulvic acids), the diagnostic tool displays a significant colour change in combination with an organic precipitate of relatively reduced proportions (sample on the right in FIG. 4).

While the presently preferred embodiments have been described for purposes of this disclosure, changes and modifications will be apparent to those of ordinary skill in the art. Such changes and modifications are encompassed within this invention as defined by the claims.

The invention claimed is:

1. A semi-quantitative diagnostic tool adapted to indicate the presence of organic residues in a product sample wherein the diagnostic tool includes a colorimetric indicator which is adapted to undergo a colour change when brought into contact with organic residues, the diagnostic tool comprising— a permanganate-based colorimetric indicator formulation comprising a dry permanganate compound, wherein the dry permanganate compound is stabilized with a chemically inert anhydrous polyphosphate and/or orthophosphate stabilizer compound and a hydroxide-based buffer compound, and wherein the quantity of dry permanganate compound in the permanganate-based formulation is predetermined such that a particular colour reaction is standardized according to a concentration of organic residues in the product sample; and a translucent assay container for containing the permanganate-based colorimetric indicator formulation;

the diagnostic tool being characterized therein that the permanganate-based colorimetric indicator formulation is admixed with a fixed sample volume of the product sample in the assay container so that the admixed permanganate-based colorimetric indicator formulation undergoes a colorimetric reaction in the presence of organic residues in the product sample; and the diagnostic tool further being characterized therein that intensity of the colorimetric reaction displayed when an organically soiled product sample is admixed with the permanganate-based colorimetric indicator formulation provides a semi-quantitative determination of a concentration of organic residue dissolved or suspended in the product sample.

2. The diagnostic tool according to claim 1 wherein the diagnostic tool is used to indicate the presence of organic residues in food, beverage and pharmaceutical manufacturing, processing and packaging equipment.

3. The diagnostic tool according to claim 1 wherein the diagnostic tool is used to indicate the presence of organic residues in water contaminated with biofilm.

4. The diagnostic tool according to claim 3 wherein the diagnostic tool is used to indicate the presence of organic residues from biofilm in prepared rinse water, prior to its use as a final rinse solution after both CIP and SIP procedures, the diagnostic tool being particularly useful to indicate the presence of EPS found in biofilms, as well as further components associated with an EPS matrix, including polysaccharides, cellulose, glycerol, glycerine and proteins.

5. The diagnostic tool according to claim 1 wherein the diagnostic tool includes a cationic sequestering agent, such as calcium.

6. The diagnostic tool according to claim 5 wherein the permanganate-based colorimetric indicator formulation is prepared under alkaline conditions and includes equal concentrations of cationic sequestering agent and dry permanganate compound.

7. The diagnostic tool according to claim 1 wherein the dry permanganate compound is formulated with one, or a combination of, potassium permanganate ($KMnO_4$), ammonium permanganate ($NH_4MnO_4$), calcium permanganate ($Ca(MnO_4)_2$), sodium permanganate ($NaMnO_4$), and/or silver permanganate ($AgMnO_4$); and preferably the permanganate compound is formulated with potassium permanganate ($KMnO_4$).

8. The diagnostic tool according to claim 1 wherein the permanganate-based colorimetric indicator formulation is compressed into a pellet or tablet form before it is introduced into the assay container and packaged in suitable packaging.

9. The diagnostic tool according to claim 1 wherein the chemically inert anhydrous polyphosphate and/or orthophosphate stabilizer compound is one, or a combination of, potassium dihydrogen orthophosphate and/or disodium hydrogen orthophosphate.

10. The diagnostic tool according to claim 1 wherein the hydroxide-based buffer compound is one, or a combination of, sodium hydroxide, magnesium hydroxide and/or potassium hydroxide.

11. The diagnostic tool according to claim 1 wherein the assay container has a fixed sampling volume of 100 ml.

12. The diagnostic tool according to claim 1 wherein the quantity of dry permanganate compound in the permanganate-based colorimetric indicator formulation is predetermined so as to yield particular and repeatable colour reactions when exposed to fixed concentrations of organic residues in a product sample.

13. The diagnostic tool according to claim 12 wherein the colour reaction of the permanganate-based colorimetric indicator formulation is reliably predictable and repeatable in view of the fact that the volume of product sample is prescribed by the fixed volume of the assay container and a proportionately measured dose of permanganate-based colorimetric indicator formulation is added to each assay container.

14. The diagnostic tool according to claim 1 wherein the permanganate-based colorimetric indicator formulation is stored under conditions of reduced temperature and a dark environment; and preferably under temperature conditions of less than 10° C.; more preferably under temperature conditions of less than 4° C.

15. The diagnostic tool according to claim 1 wherein the permanganate-based colorimetric indicator formulation excludes all organic compounds.

16. The diagnostic tool according to claim 1 wherein the diagnostic tool includes a standard colour chart illustrating a series of colour reactions wherein each colour reaction corresponds to a specific concentration of organic residue in a product sample, the arrangement being such that once a product sample is brought into contact with the permanganate-based colorimetric indicator formulation, the intensity of the resultant colour reaction is directly contrasted against the colour chart to diagnose a semi-quantitative concentration of organic residue present in the product sample.

17. The diagnostic tool according to claim 16 wherein the diagnostic tool includes a set of standard colour charts with each colour chart illustrating a series of colour reactions and wherein different colour charts correspond to different concentrations of organic material encountered in different applications in the food, beverage and pharmaceutical industry, the arrangement being such that for each concentration of organic material the intensity of a colour reaction when that product sample is brought into contact with the permanganate-based colorimetric indicator formulation is directly contrasted against the colour chart for that particular concentration of organic material to diagnose a semi-quantitative concentration of organic material present.

18. The diagnostic tool according to claim 1 wherein the diagnostic tool includes an untreated control comprising an assay container and including the permanganate-based colorimetric indicator formulation, wherein the permanganate-based colorimetric indicator formulation is admixed with a volume of demineralized water of known purity to undergo a colorimetric reaction, the arrangement being such that the colorimetric reaction displayed when a product sample is admixed with the permanganate-based formulation of a test assay is contrasted against the colorimetric reaction of the untreated control to determine the presence of organic residues in the product sample.

19. The diagnostic tool according to claim 1 wherein the diagnostic tool is adapted to diagnose a concentration of organic residues in a product sample of as low as ≤1 ppm.

20. The diagnostic tool according to claim 1 wherein the diagnostic tool is adapted such that after 5 minutes from the time when an organically soiled product sample is admixed with the permanganate-based colorimetric indicator formulation, a resultant colorimetric reaction will reliably diagnose a concentration of organic residues in a product sample of as low as ≤1 ppm.

21. A permanganate-based colorimetric indicator formulation which is adapted to undergo a colour change when brought into contact with organic residues in a product sample, the permanganate-based colorimetric indicator formulation comprising a dry permanganate compound, wherein the dry permanganate compound is stabilized with a chemically inert anhydrous polyphosphate and/or orthophosphate stabilizer compound and a hydroxide-based buffer compound, and wherein the quantity of dry permanganate compound in the permanganate-based formulation is predetermined such that a particular colour reaction is standardized according to a concentration of organic residues in the product sample.

22. The permanganate-based colorimetric indicator formulation according to claim 21 wherein the permanganate-based colorimetric indicator formulation is used to indicate the presence of organic residues in food, beverage and pharmaceutical manufacturing, processing and packaging equipment.

23. The permanganate-based colorimetric indicator formulation according to claim 21 wherein the permanganate-based colorimetric indicator formulation is used to indicate the presence of organic residues derived from biofilm in water.

24. The permanganate-based colorimetric indicator formulation according to claim 23 wherein the permanganate-based colorimetric indicator formulation is used to indicate the presence of organic residues derived from biofilm in prepared rinse water, prior to its use as a final rinse solution after both CIP and SIP procedures, the formulation being particularly useful to indicate the presence of EPS found in biofilms, as well as further components associated with an EPS matrix, including polysaccharides, cellulose, glycerol, glycerine and proteins.

25. A method of obtaining a semi-quantitative indication of the presence of organic residues in a product sample, the method comprising the steps of providing a diagnostic tool comprising — a permanganate-based colorimetric indicator formulation comprising a dry permanganate compound, wherein the dry permanganate compound is stabilized with a chemically inert anhydrous polyphosphate and/or orthophosphate stabilizer compound and a hydroxide-based buffer compound, and wherein the quantity of dry permanganate compound in the permanganate-based colorimetric indicator formulation is predetermined such that a colour reaction is standardized according to a concentration of organic residues in a product sample; and a translucent test assay container for containing the permanganate-based colorimetric indicator formulation, providing either one or both of a standard colour chart on which a series of colour reactions each correspond to a concentration of organic residue, and/or an untreated control;

collecting a fixed sample volume of product sample and admixing it with the permanganate-based colorimetric indicator formulation in the test assay container such that the permanganate-based colorimetric indicator formulation undergoes a colorimetric reaction in the presence of organic residues in the product sample; and contrasting presence and/or intensity of the colorimetric reaction against either one or both of the colour chart or untreated control to diagnose a semi-quantitative concentration of organic residue present in the product sample.

26. The method according to claim 25 wherein the method includes the step of collecting product sample from food, beverage and/or pharmaceutical manufacturing, processing and packaging equipment after a CIP process or cycle and before the step of introducing a SIP process or cycle so as to verify the efficacy of the CIP process or cycle as mandated by a specific food and/or beverage producer.

27. The method according to claim 25 wherein the method, alternatively or additionally, includes the step of collecting product sample from prepared rinse water, particularly prior to its use as a final rinse solution after both CIP and SIP procedures, so as to indicate the presence or absence of EPS as found in biofilms, as well as further components associated with an EPS matrix, such as polysaccharides, cellulose, glycerol, glycerine and proteins.

28. Use of a diagnostic tool according to claim 1 for detecting and semi-quantifying organic residues in rinse effluent in food, beverage and pharmaceutical manufacturing, processing and packaging applications, systems and equipment.

29. The use according to claim 28 wherein the diagnostic tool is used for detecting and semi-quantifying organic residues in rinse effluent in systems and equipment for processing brewed beverages, fermented beverages, fruit and vegetable beverages, tea and coffee beverages, flavoured water products, carbonated soft drinks, sport drinks, combinations thereof, or pharmaceuticals and particularly for detecting a presence of potent oxidising chemical residues in rinse effluent in food, beverage and pharmaceutical manufacturing, processing and packaging applications, systems and equipment.

30. Use of a diagnostic tool according to claim 1 for verifying cleaning procedures of "point-of-use" beverage dispensers installed in, but not limited to, retail outlets and equivalent hospitality venues.

31. Use of a diagnostic tool according to claim 1 for indicating the presence of organic residues from biofilm in prepared rinse water, the diagnostic tool being particularly useful to indicate the presence or absence of EPS found in biofilms from prepared rinse water, prior to its use as a final rinse solution after both CIP and SIP procedures, as well as further components associated with an EPS matrix, including as polysaccharides, cellulose, glycerol, glycerine and proteins.

32. The use according to claim 31 wherein the diagnostic tool is used to verify efficacy of both CIP and SIP procedures to remove residual organic soils specifically associated with food, beverage and pharmaceutical products.

33. The use according to claim 31 wherein the diagnostic tool is used to indicate the presence or absence of EPS found in biofilms from prepared rinse water, as well as further components associated with an EPS matrix, including polysaccharides, cellulose, glycerol, glycerine and proteins, both before and after CIP and SIP procedures in order to exclude "false-positive" results that arise as a result of secondary soiling of the manufacturing, processing and packaging equipment with biofilm contaminated rinse water.

34. Use of a diagnostic tool according to claim 1 for precipitating organic contaminants from a water sample such that the extent of organic precipitate is an indication of the type of and molecular mass of organic contaminants present in the water sample.

* * * * *